June 15, 1976 R. G. JELLY Plant Pat. 3,914
ROSE PLANT NAMED FESTIVE
(SEEDLING #8-69-RS)
Filed July 7, 1975
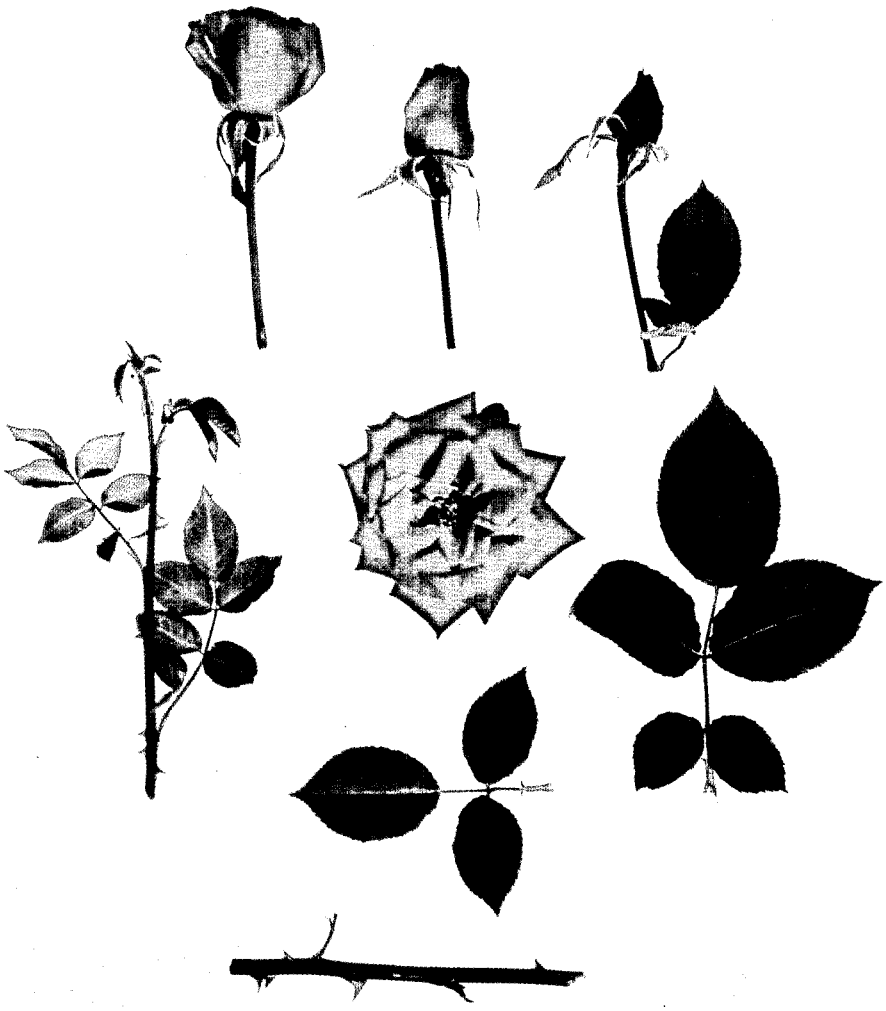

United States Patent

Plant Pat. 3,914

Patented June 15, 1976

3,914

ROSE PLANT NAMED FESTIVE

Robert G. Jelly, Richmond, Ind., assignor to E. G. Hill Co., Inc., Richmond, Ind.

Filed July 7, 1975, Ser. No. 593,731

Int. Cl. A01h *5/00*

U.S. Cl. Plt.—29 1 Claim

ABSTRACT OF THE DISCLOSURE

A new variety of rose plant of the floribunda type for greenhouse culture and production of cut flowers, distinguished by its lustrous dark red blooms, its extraordinary upright growth and uniformity of cane, the absence of blind wood, and its superior wintertime productivity.

BACKGROUND OF THE NEW PLANT

This new variety of rose plant originated as a seedling resulting from my crossing of Baccara (Plant Pat. No. 1,367) with Rose #47-65-R from my stock of breeding plants maintained in Richmond, Ind., this crossing having been made by me at Richmond, Ind., in the autumn of 1967 with the object of improving upon the color and winter productivity of the seed parent Baccara while maintaining the good growth characteristics of the pollen parent and eliminating the presence of blind wood.

The first flower was produced in April of 1968 and it soon became apparent that the objectives had become accomplished in the new plant whereupon propagation by grafting was begun under my direction at Richmond, Ind., and by budding at Livermore, Calif., and successive propagations of the new plant, both at Richmond, Ind. and at Livermore, Calif., have demonstrated that the distinctive characteristics of this new variety hold true from generation to generation and are firmly fixed.

DESCRIPTION OF THE DRAWING

Distinctive features of my new variety are illustrated by the accompanying full color photographically produced drawing in which several stages of the buds are shown together with a face view of a fully opened flower, a top side view of a mature leaf and an under side view of a younger leaf, the drawing also showing a piece of the mature wood and a cutting showing the wood and foliage of a very young plant. The colors shown are as nearly true as it is reasonably possible to obtain by professional photographic procedures.

DESCRIPTION OF THE NEW PLANT

The following is a detailed description of my new rose plant variety with color designations according to the R.H.S. Colour Chart (RHS) and the Horticultural Colour Chart by Robert S. Wilson (W), both charts being published by The Royal Horticultural Society at London, England, in conjunction with the British Colour Council.

The plant

Origin: Seedling.

Parentage: Seed parent—Baccara (Plant Pat. No. 1,367); pollen parent—#47-65-R.

Classification: Botanic—hybrid rose; commercial—floribunda.

Form: Bush.

Habit: Upright and much branched.

Growth: Vigorous and moderately free.

Canes: Of medium diameter.

Main steams:

*Color.*—Shaded from Yellow Green 147B to 146B (RHS).

*Thorns.*—Few to several, medium in length and hooked slightly downward from a long, narrow base. Color: Greyed Orange 167D (RHS).

*Prickles.*—Few. Color: Greyed Orange 165C (RHS).

*Hairs.*—None.

Branches:

*Color.*—Green 137C (RHS) mottled with Yellow Green 144C (RHS).

*Thorns.*—Several, short to medium in length, hooked slightly downward from a short, narrow base. Color: Shaded from Greyed Purple 184D (RHS) to almost translucent at the tip.

*Prickles.*—Few, almost translucent in color.

*Hairs.*—None.

Foliage:

*Quantity.*—Abundant.

*Leaves.*—Compound and odd pinnate, normally of medium size.

*Leaflets.*—3 or 5 and sometimes 7 in number. Shape: Ovate with a cuspidate apex, an obtuse or rounded base, and a simply serrate margin. Color: Mature leaves—upper surface—Parsley Green 00962 (W); under surface—Lavender Green shaded from 00761 to 00761/1 (W). Young leaves—upper surface—slightly more dull than Greyed Purple 187A (RHS) with venation varying from Fern Green 0862 (W) to 0862/1 (W); under surface—general color of Greyed Red 182D (RHS) with venation shades of Yellow Green 144C and 144D (RHS). Texture—thick and leathery. Aspect—glossy.

*Rachis.*—Medium in length and size. Upper side: Grooved and prickly. Under side: Slightly thorny.

*Stipules.*—Moderately short, very narrow, with moderately short points turning out at an angle of 45° and not recurving toward the stem.

The bud

Before calyx breaks:

*Size.*—Medium small.

*Form.*—Short pointed to globular with a conspicuous neck and with foliaceous appendages on the surface of the bud having foliaceous parts extending beyond the bud tip for about ¼ of the bud length.

*Color* of *calyx.*—Yellow Green 144A (RHS).

As calyx breaks:

*Outside petal color.*—Greyed Purple 187A (RHS).

As first petal opens:

*Bud size and form.*—Medium large, short pointed to flat.

*Color.*—Outside of petal—slightly darker than Red 53B (RHS); inside of petal—more brilliant than Red 53A (RHS).

Bud opening: Bud opens very well in greenhouse. During hot, dry weather, there is a slight decrease in bud size and a slightly lighter color intensity.

Sepals: Permanent, of medium length, spear shaped curving backward and downward as bud begins to open up.

*Inside color.*—Yellow Green 145B (RHS) at the base to shades between Green 143A and 143B (RHS).

*Outside color.*—Green 143C (RHS).

Peduncle: Short to medium in length, strong and erect.

*Bark.*—Entirely smooth. Color: Yellow Green 144A (RHS).

The flower

Blooming habit: Free, abundant and continuous in greenhouse.

Borne: Several to each stem, on strong stems of long length.

Size: Medium large—3 to 3½ inches in diameter when fully opened.

Form: High centered at first, becoming flat to high centered as bloom matures. At first the petals remain tightly rolled outward, becoming loosely rolled outward at maturity.

Petalage: Very double, with 27 to 32 petals arranged regularly.

*Shape.*—Outside petals—oval with cuspidate apex. Intermediate petals—oval to slightly obovate with apex slightly cuspidate. Inside petals—oval to obovate with cuspidate apex.

*Texture.*—Moderately thick and leathery.

*Aspects.*—Inside—velvety; outside—satiny.

Color: The colors stated may be modified by being shaded with other colors.

(A) The following description is from observation of a flower of my improved rose plant grown in greenhouse at Richmond, Ind., and newly opened in the month of December 1974.

Outside petals:

*Outer surface.*—From Yellow 1D to 4D (RHS) at the base to slightly darker than a shade from Red 53B to 53C (RHS).

*Inside surface.*—Shaded from Yellow 4C to 4D (RHS) at the base to a shade of Red 46A (RHS) and Current Red 821 (W) but darker than both.

Intermediate petals:

*Outer surface.*—Shaded from Yellow 2D to Yellow 4D (RHS) at base to Red 53C (RHS) which is the main color.

*Inside surface.*—Shaded from Yellow 2D to Yellow 4D (RHS) at base to a shade slightly darker than Red 46A and 46B (RHS), the main color.

Inner petals:

*Outer surface.*—A shade of Red 53B and Red 53C (RHS). Some petals show a streak of White 155B (RHS) from base to top.

*Inside surface.*—From Yellow 4D (RHS) at the base to slightly darker than a shade of Red 46A to a shade of 46B (RHS).

(B) The following is from observation of a flower of my new rose plant, grown in greenhouse at Richmond, Ind., that was opened for three days in February 1975.

Outside petals:

*Outer surface.*—Yellow 2C (RHS) at the base to Red Purple 57C (RHS) shaded to a little darker than Red 53C (RHS).

*Inside surface.*—Yellow 2D (RHS) to White 155C (RHS) shaded to Red Purple to the main color which is a shade between Red 53A (RHS) and Cardinal Red 822/1 (W).

Intermediate petals:

*Outer surface.*—Green Yellow 1D (RHS at the base shaded to the main color which is slightly darker than Cherry 722/1 (W).

*Inner surface.*—Yellow 4D (RHS) at the base to Red Purple 62A (RHS) to a main color a shade between Red 46A to 46B (RHS).

Inner petals:

*Outside surface.*—Yellow 4D (RHS) at the base to a main color of Rose Red 724 (W).

*Inside surface.*—Yellow 8D (RHS) at the base shaded through Red Purple 57D to a main color a shade between Red 46A and Red 46B (RHS).

General color effect:

*Newly opened flower.*—From Red 53A (RHS) to Red 46A (RHS).

*Three days open.*—Slightly darker than Red 46B (RHS).

Behavior of petals in greenhouse: The petals persist and are affected by hot, dry weather by the color fading from Red 46C to 46D (RHS).

Flower longevity: 7 days at living room temperature in February 1975.

Fragrance (in greenhouse): Slightly sweetbriar.

Reproductive organs

Stamens: Medium in number arranged regularly about the pisitals, mixed with a few petaloids.

*Anthers.*—Medium small, most of them open at once. Color: Yellow 11C (RHS) in the center of the pollen cup to a shade of Yellow Orange Yellow 22A and 22B (RHS) on the margin.

*Filaments.*—Short and long, most with anthers. Color: Yellow 12A (RHS) at the base to Red 45D (RHS), the main color.

*Pollen.*—Abundant. Color: Yellow Orange 22B (RHS).

Pistils: Number—medium.

*Styles.*—Slightly uneven and of medium length, moderately thin and bunched. Color: Yellow Green 150D (RHS) at the base to Red 46B (RHS) under the stigma. Stigma color: Slightly lighter than Yellow Orange 20C (RHS).

Ovaries: Some protruding from the calyx.

Hips: Medium length, ovoid to globular or gourd shaped in form, with conspicuous neck and with rough, moderately thick, fleshy walls.

*Color.*—Shades of Green 143B and Green 143C (RHS) at the top and base with the main body Orange 25A (RHS).

Seeds: Many, of medium size, and some protruding.

My new variety of rose plant is an improvement over its seed parent, Baccara, in that it is red rather than orange red and has superior wintertime productivity. The size of the bloom makes the plant a floribunda rather than a hybrid tea. This new plant has marvelous upright growth and uniformity of cane, topped by a lustrous dark red bloom, and is superior to the pollen parent, undisseminated seedling 47–65–R, in that the good growth characteristic of the pollen parent has been maintained and the presence of blind wood has been substantially eliminated.

I claim:

1. A new and distinct variety of rose plant substantially as herein shown and described, characterized by its continuous production of lustrous dark red blooms on strong, long, upright stems and strong erect peduncles of medium length, its vigorous and moderately free growth habit with almost complete elimination of blind wood, and its superior wintertime productivity.

No references cited.

ROBERT E. BAGWILL, Primary Examiner